US008220617B2

(12) United States Patent
Eberle

(10) Patent No.: US 8,220,617 B2
(45) Date of Patent: Jul. 17, 2012

(54) DEVICE FOR FEEDING SAMPLE CONTAINERS WITH AN ANALYSIS SAMPLE TO A TREATING APPARATUS

(75) Inventor: Klaus-Gunter Eberle, Tuttlingen (DE)

(73) Assignee: Andreas Hettich GmbH & Co. KG, Tuttlingen (DE)

( * ) Notice: Subject to any disclaimer, the term of this patent is extended or adjusted under 35 U.S.C. 154(b) by 525 days.

(21) Appl. No.: 12/490,308

(22) Filed: Jun. 23, 2009

(65) Prior Publication Data
US 2009/0324370 A1 Dec. 31, 2009

(30) Foreign Application Priority Data
Jun. 30, 2008 (DE) .................. 10 2008 030 330

(51) Int. Cl.
B65G 43/00 (2006.01)
(52) U.S. Cl. ............. 198/571; 198/575; 198/465.2; 198/370.02; 198/346.2
(58) Field of Classification Search ............. 198/571, 198/575, 465.2, 426, 370.02, 346.2
See application file for complete search history.

(56) References Cited

U.S. PATENT DOCUMENTS

| | | | | | |
|---|---|---|---|---|---|
| 3,595,366 | A | * | 7/1971 | Johanski | 198/468.6 |
| 3,759,227 | A | * | 9/1973 | Wolfe et al. | 119/57.7 |
| 3,796,327 | A | * | 3/1974 | Meyer et al. | 414/222.02 |
| 3,985,222 | A | * | 10/1976 | Kressly | 198/617 |
| 4,359,149 | A | * | 11/1982 | Erlichman et al. | 198/347.1 |
| 4,369,563 | A | * | 1/1983 | Williamson | 483/7 |
| 4,991,706 | A | * | 2/1991 | Kitamura | 198/346.1 |
| 5,402,875 | A | * | 4/1995 | Markin et al. | 198/346.1 |
| 6,139,240 | A | * | 10/2000 | Ando | 414/267 |
| 6,189,702 | B1 | * | 2/2001 | Bonnet | 209/651 |
| 6,321,138 | B1 | * | 11/2001 | Livesay et al. | 700/245 |
| 6,578,614 | B1 | * | 6/2003 | Loewenthal | 156/358 |
| 6,688,451 | B2 | * | 2/2004 | Derby et al. | 198/346.1 |
| 6,745,454 | B1 | * | 6/2004 | Grimshaw et al. | 29/563 |

(Continued)

FOREIGN PATENT DOCUMENTS
DE 3644024 A1 6/1988
(Continued)

Primary Examiner — Joseph A Dillon, Jr.
(74) Attorney, Agent, or Firm — Woodling, Krost and Rust

(57) ABSTRACT

The invention provides a device (10) for feeding sample containers (18) with an analysis sample (P) to be treated, to a treating apparatus (12) for treating the analysis sample (P), in particular to a centrifuge. The device comprises a conveyer (26, 27) for conveying at least one sample container (14) or at least one carrier containing a sample container (14), wherein the conveyer (26, 27) is configured for receiving multiple sample containers (14) and/or carriers and forms a circulating endless conveyer track. The device further comprises an input station (18) for handing over a sample container (14) or a carrier to the conveyer (26, 27). The input station (18) is displaced (V1, V2), with respect to the conveyer (26, 27), obliquely to the conveying direction (26b, 27b) Hof the conveyer (26, 27). A removal station (20) is for removing the sample container (14) or the carrier out of the conveyer (26, 27), and a transfer device (44) serves for removing the sample container (14) or the carrier with the sample container (14) out of the conveyer (26, 27) for further transport to the treating apparatus (12) and for a hand over to the conveyer (26, 27) after the treatment of the analysis sample (P) of the sample container (14) in the treating apparatus. An identification unit (48) is provided for identifying a sample container (14).

18 Claims, 4 Drawing Sheets

U.S. PATENT DOCUMENTS

| | | | |
|---|---|---|---|
| 6,854,583 B1 * | 2/2005 | Horn | 198/348 |
| 6,999,847 B2 * | 2/2006 | Barry et al. | 700/213 |
| 7,168,548 B2 * | 1/2007 | Naumann et al. | 198/346.2 |
| 7,233,838 B2 * | 6/2007 | Barry et al. | 700/213 |
| 7,569,794 B2 * | 8/2009 | Faour et al. | 219/121.68 |
| 7,958,987 B2 * | 6/2011 | Monti | 198/357 |

FOREIGN PATENT DOCUMENTS

| | | |
|---|---|---|
| DE | 68915648 T2 | 2/1990 |
| DE | 10041230 A1 | 3/2002 |
| EP | 1003020 A1 | 5/2000 |
| EP | 1662261 A1 | 5/2006 |

* cited by examiner

DEVICE FOR FEEDING SAMPLE CONTAINERS WITH AN ANALYSIS SAMPLE TO A TREATING APPARATUS

This patent application claims priority to German patent application no. 10 2008 030 330.5 filed Jun. 30, 2008.

The invention relates to a device for feeding sample containers with an analysis sample to be treated, to a treating apparatus where the samples are treated.

BACKGROUND OF THE INVENTION

Devices for feeding sample containers with an analysis sample to a treating apparatus for treating the analysis sample, in particular by means of a centrifuge, are already known for a long time. In the known implementation of this device, an input station from which a conveyer in the form of a conveyer belt for the sample containers or carriers, extends to a transfer device for transferring the sample containers to the device. The transfer device picks the sample containers or carriers of the conveyer belt and feeds them to the treating apparatus.

Each sample container or carrier comprises an identification which relates to the analysis sample and the related treatment thereto by means of the treating apparatus. Before the sample containers with an analysis sample or the carriers are fed by means of the transfer device to the treating apparatus, they are detected by a reading unit arranged behind the input station. The reading unit detects the respective identification of the sample containers or carriers by reading out the measures to be carried out therewith or the treatments, respectively. The data are fed to a control unit. Thereafter, the sample container with the respective analysis sample or the carrier with the sample container and the analysis sample contained therein is introduced into the treatment apparatus, for example into a centrifuge. In the treating apparatus, the analysis sample positioned in the sample container is treated, for example centrifuged, according to the method steps specified by the control unit and associated with the sample container and, thereby, to the analysis sample.

Thereafter, the sample container or the carrier with the sample container is again taken off the treating apparatus by the transfer device and transferred to a second conveyer belt. The second conveyer belt conveys the sample containers or carriers to a removal station where the sample containers can be taken off by hand.

A carrier comprises at least one sample container with an analysis sample. However, carriers having several sample containers are usual.

In the known device, the sample containers or the carriers can only be treated by the treating apparatus and conveyed by the two conveyer belts according to the sequence in which they are input into the input station. The sample containers or carriers can also only be removed again at the removal station one after another according to this sequence.

It is disadvantageous in these known devices that the sequence is compulsively determined by the sequence of the input. A treating according to priorities and pooling of sample containers or carriers to be treated in the same way, is not possible in the treating apparatus.

From DE 100 41 230 A1, a device for treating objects, in particular cytological or histological specimens, is known. The disclosed device comprises multiple processing stations and a transport device for delivering the objects into and out of the processing stations, wherein a loading station for loading with objects to be treated or with object carriers carrying the objects to be treated, and a removal station for removing the treated objects or objects carriers carrying the treated objects, are provided. The device is characterized thereby that a definable number of processing stations can be allocated in a fixed or variable fashion to the loading station and/or the removal station.

It is also a further problem with the known device that sample containers with an analysis sample or carriers get into the conveyer circulation, the identification of which has not been read correctly or not read at all and which can, therefore, not be treated, can adversely effect and block the throughput. The throughput of the device as well as of the treating apparatus is substantially adversely affected thereby.

SUMMARY OF THE INVENTION

It is an object of the invention to increase the throughput of a device for feeding sample containers with an analysis sample to be treated, to a treating apparatus where the samples are treated.

According to an aspect of the invention, a device for feeding sample containers with an analysis sample to be treated, to a treating apparatus for treating the analysis sample, in particular a centrifuge, comprises a conveyer for conveying at least one sample container or at least one carrier containing a sample container; an input station for handing over a sample container or a carrier to the conveyer; a removal station for removing the sample container or the carrier out of the conveyer; a transfer device for removing the sample container or the carrier with the sample container out of the conveyer for further transportation to the treating apparatus and for a handover to the conveyer after the treatment of the analysis sample of the sample container in the treating apparatus; an identification unit for identifying a sample container, wherein the conveyer is configured for receiving multiple sample containers and/or carriers and forms a circulating endless conveyer track; and wherein the input station is displaced with respect to the conveyer obliquely to the conveying direction of the conveyer.

The invention is based on the finding that the throughput of the device can be increased by quickly removing untreatable sample containers, for example because of wrong identification with a correctly readable sample container, out of the device.

The device of the invention ensures in an advantageous way that a sample container or carrier which is not identified at the input station and which is not further conveyed can be removed from the input station in a simple way. The user immediately recognizes the faulty identification or the bad orientation of the sample with respect to the identification unit. Thereby, a conveyer is kept free in a simple way of sample containers which are not identifiable or the identification of which containers is not in order.

According to an embodiment of the invention, at least two conveyers are provided. Thereby, the throughput can be considerably increased. During unloading or loading of one conveyer, conveying can already be carried out by the further conveyer. This results in a considerable increase in efficiency.

Preferably, a first conveyer runs, for example, from the input station to the transfer device, and a second conveyer can run from the transfer device to the removal station.

Preferably, the conveyer comprises receiving means for receiving single sample containers or carriers of sample containers. Thereby, the sample container or carrier can be moved into and out of the receiving means in a simple way. The receiving means for the sample containers or carriers can, above all, be arranged in a line.

It is a further objective that only sample containers or carriers which have been positively identified before, get into the conveyer circulation and into the treating apparatus.

According to a further embodiment, a transfer conveyer for conveying a sample container transferred to the input station, to the conveyer at which the identification unit is arranged in the area of the transfer conveyer and cooperates with the transfer conveyer such that the sample container or carrier is conveyed to the conveyer only after its identification.

Thereby, it is ensured that only such sample containers get into the conveyer circulations which are identified and the identification of which is known to a respective control device. Therefore, the conveying of the sample containers with an analysis sample or of the carriers can be effected undisturbed and, therefore, more efficiently in the invention.

If the input station is displaced upwards with respect to the conveyer and/or the removal station, a transfer conveyer of simple construction can be implemented, for example thereby that the second conveyer is formed by a drop-down passage and that, therefore, a complex active conveyer is dispensed with.

A larger clearance usable for handling, can also be gained for the removal station if the input station is offset in the conveying direction of the conveyer with respect to the removal station.

According to a preferred embodiment of the invention, the identification unit is arranged in conveying direction of the second conveyer in front of the conveyer, preferably in the vicinity of the input station.

A receiving means for inputting the sample containers or carriers at the input station allows an accurate positioning of the sample containers or carriers such that also the probability of identification of the sample containers or carriers is improved. Therein, the receiving means are adapted to the outer shape of the sample container or the carrier.

Preferably, the receiving means are formed by a tubular receiving part. This is easy to manufacture and can be exchanged according to the type of the sample container.

According to a further embodiment of the invention, the receiving means can be provided with a lateral window for identifying the identification of the sample container or the carrier by means of the identification unit. Thereby, the reliable allocation of the sample container or carrier as well as a simple identification by means of the identification unit is ensured. Therein, the identification unit is, above all, arranged opposite to the window.

The identification unit can, in particular, be formed by the reading unit in particular in form of a unit which can be taken off and put back again by hand.

Preferably, a holder can be provided in which the identification unit is supported to be selectively removed.

According to an embodiment of the invention, the device and the treating apparatus form a structural unit.

Further advantages, features and possibilities of use of the invention of a device for feeding sample containers with an analysis sample to be treated, can be taken from the following description in connection with the embodiment shown in the drawings.

A further understanding of the nature and advantages of the embodiments of the present invention may be realized by reference to the remaining portions of the specification and the drawings.

DESCRIPTION OF THE SPECIFIC EMBODIMENTS

Figure 1:
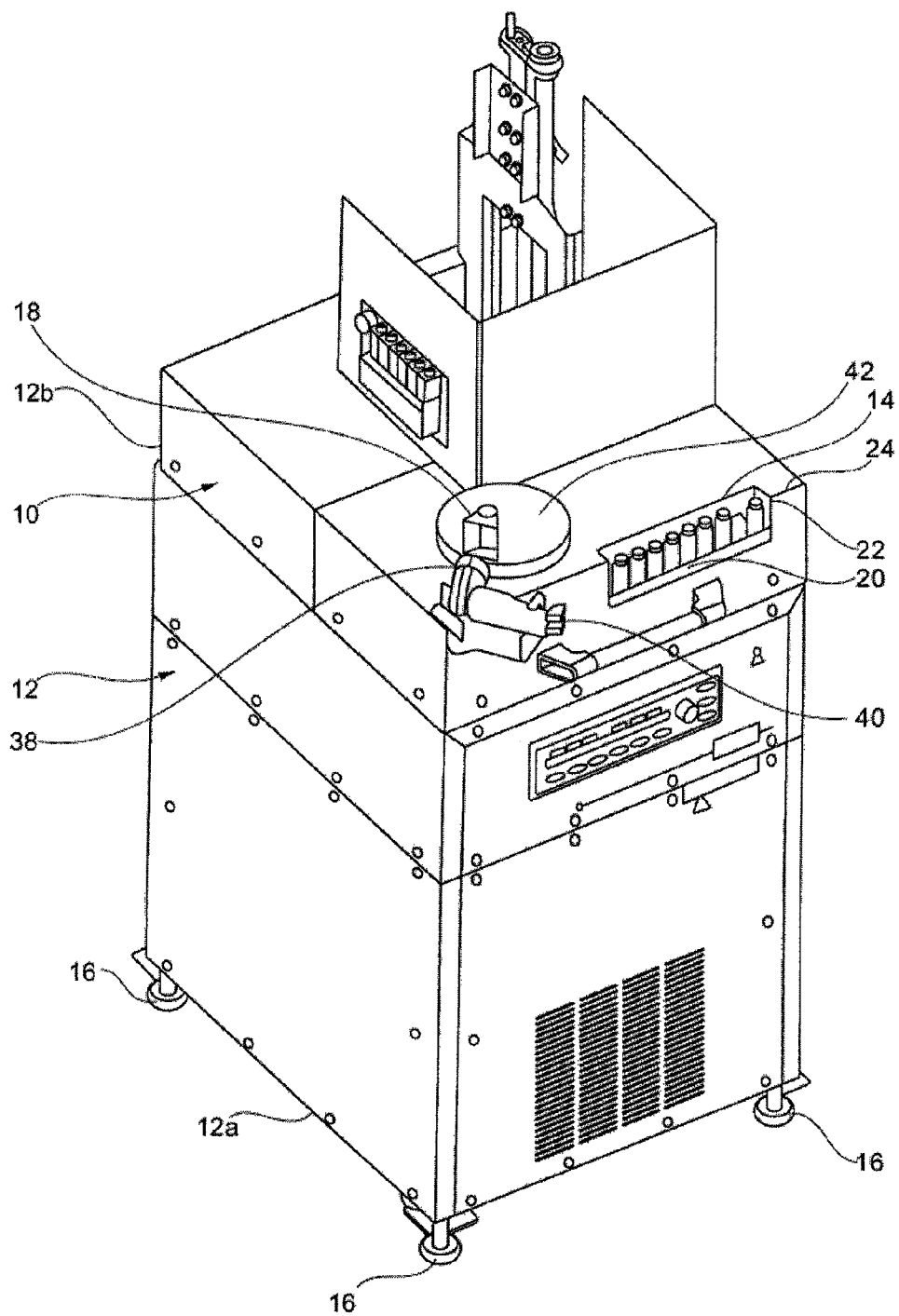
FIG. 1 is a perspective oblique top view of the device for feeding sample containers or carriers with an analysis sample to be treated, to a treating apparatus according to the invention.
Figure 2:
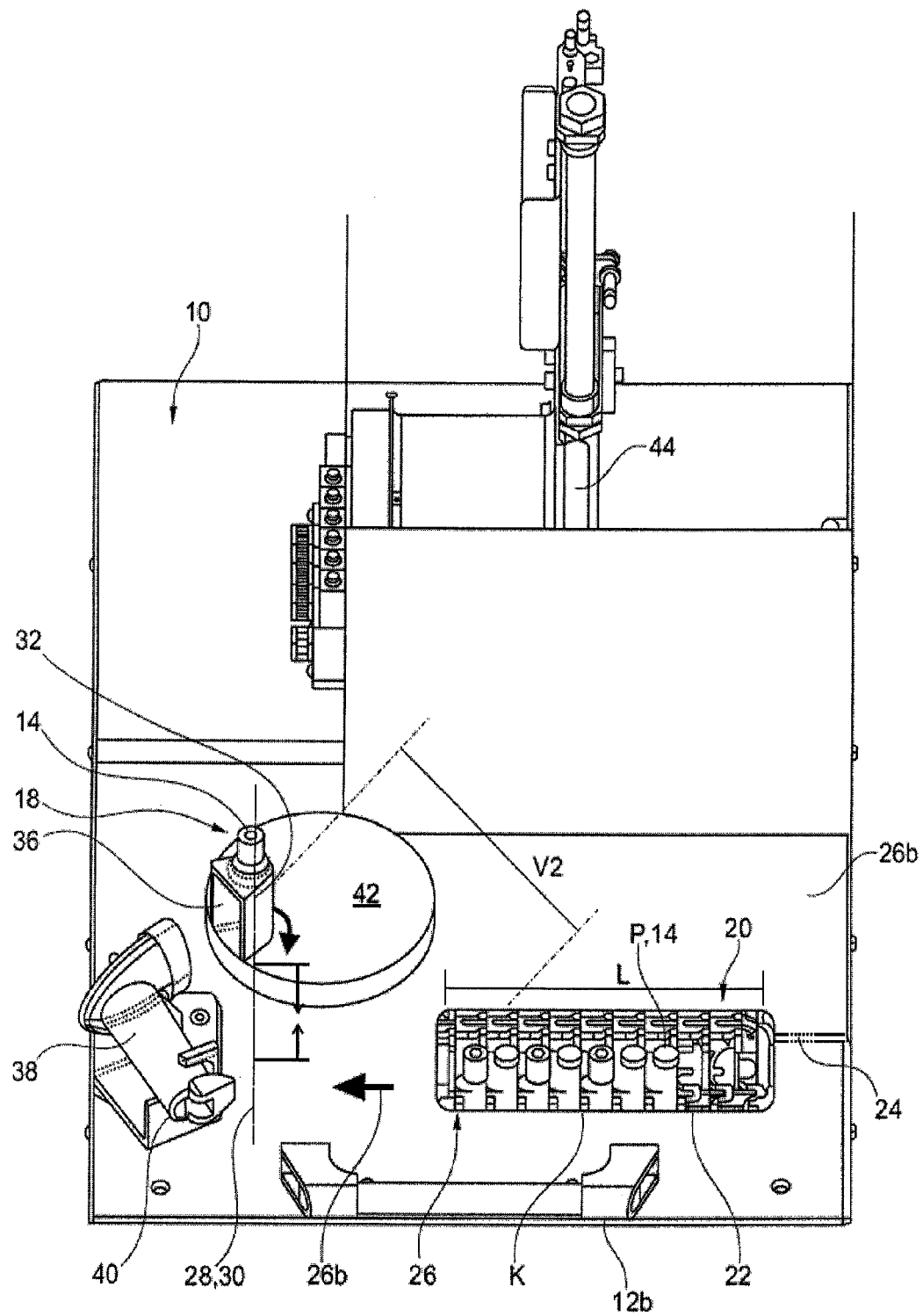
FIG. 2 is a perspective oblique top view from an intermediate point of view of the front side.
Figure 3:
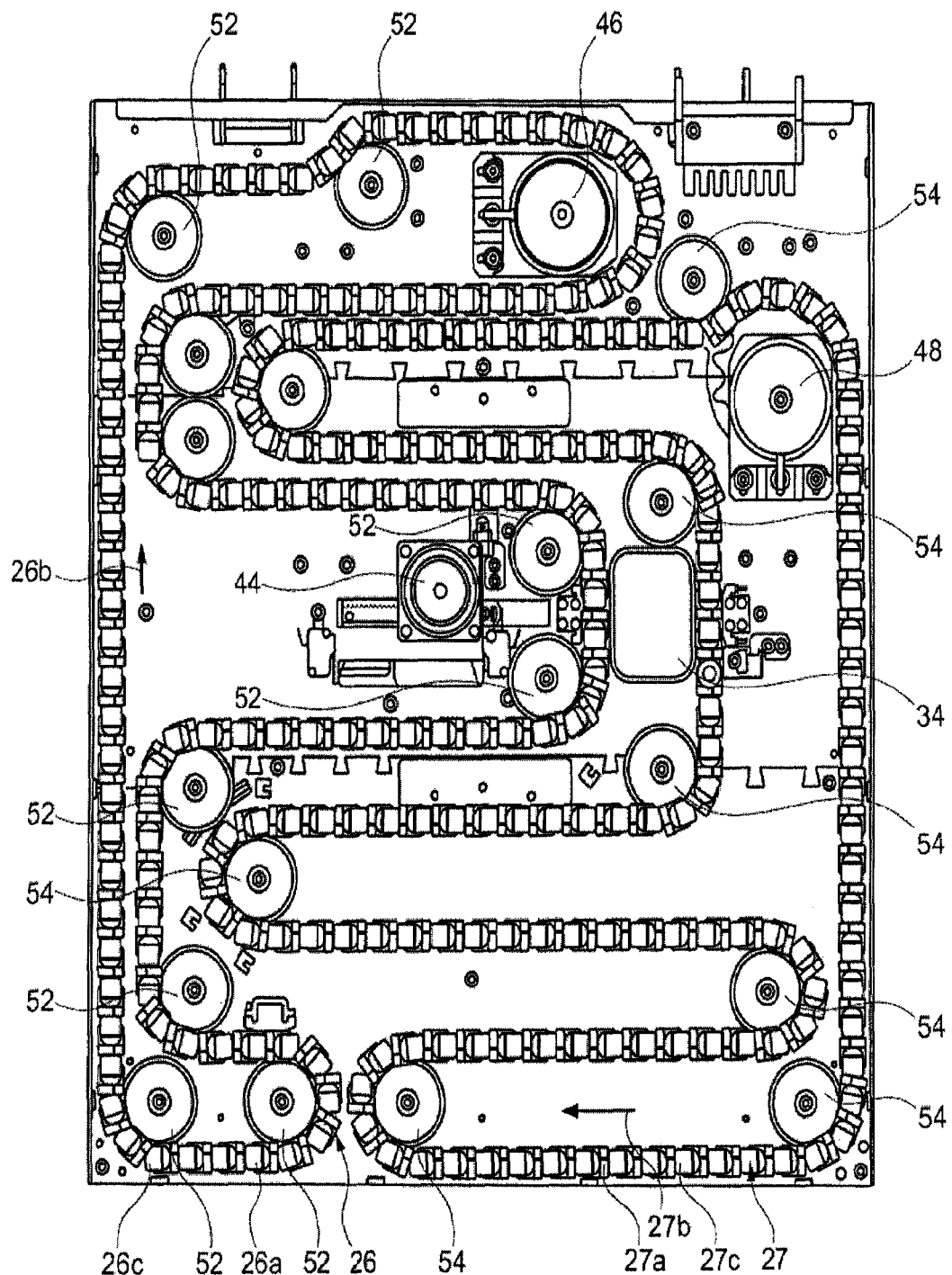
FIG. 3 is a top view onto a horizontal section of the device with the two conveyers.
Figure 4:
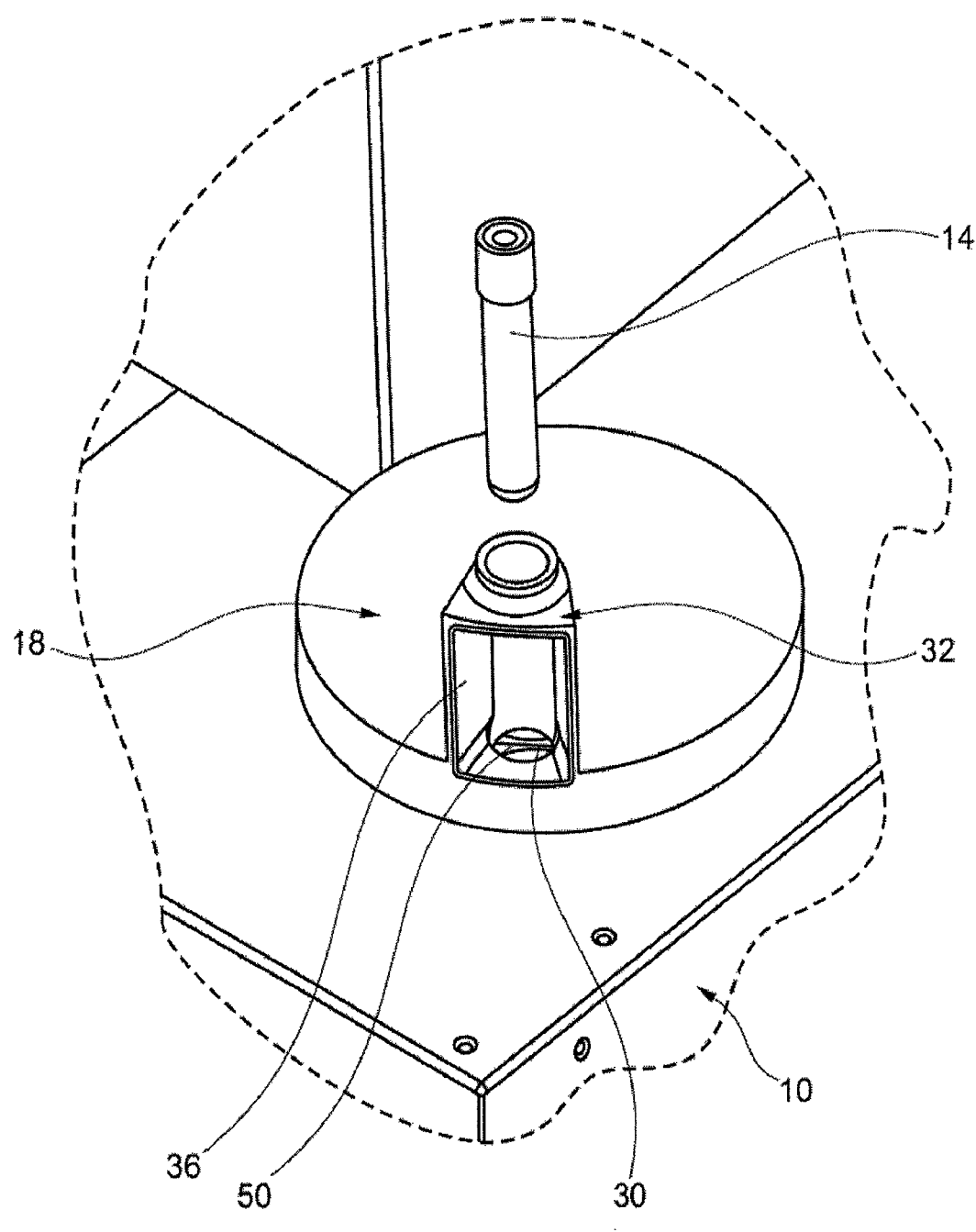
FIG. 4 is an exploded view of the input station of FIG. 2.

In the FIGS. 1 to 4, an embodiment of a device 10 according to the invention is shown which is designated in its entirety with 10. The device 10 is an integral component of the treating apparatus 12. The device 10 can also be formed as a separate top fixture. The treating apparatus 12 is, in this embodiment, a centrifuge for centrifuging and, thereby, separating of components of the analysis sample P in the sample container 14. The analysis sample P can, in particular, be formed by blood. Alternatively, the sample containers 14 can also be positioned in carriers, so called racks, which are conveyed through the device 10 to the treating apparatus 12. Therein, the carriers can contain single or multiple sample containers 14 with analysis sample P. In the following embodiment, the sample containers 14 are, however, conveyed without a carrier through the device 10 to the treating apparatus 12 and back again.

The sample container 14 with the analysis sample P to be treated, is, for example, formed by a hollow cylindrical container which is respectively closed by means of a cover. The sample containers 14 with the analysis sample P contained therein, are provided with an identification P for identifying the same. This identification is, for example, applied to the outer surface or the cylinder shell surface of the sample container 14. For example, the relationship, the kind of the analysis sample and the date may be contained in this identification K. The identification K can be implemented by a bar code.

The device 10 preferably constitutes an upper portion of the treating apparatus 12 with a housing 12a standing on legs 16 which are adjustable in height. The device 10 is, for example, a flat housing 12b which forms a cover of the housing 12a. Therein, the device 10 can be connected fixedly or permanently, respectively, or detachably to the housing 12a.

The device 10 comprises an input station 18 for loading and unloading of the sample containers 14 with an analysis sample P to be treated, and a removal station 20. Both of them are located in the front area of the device 10 for the purpose of improving the handling.

A first circulating conveyer 26 provided as endless belt runs from the input station 18 to a transfer device 44. The transfer device 44 transports the sample containers 14 into the treating apparatus 12 and, after the treatment, to a second circulating conveyer 27 formed as an endless belt. The second conveyer 27 runs from the transfer device 44 to the removal station 20.

The removal station 20 is formed by an opening 22 in the area of the upper front edge 24 of the flat housing 12b such that the opening 22 is open on top and in front. According to an alternative embodiment, this can also be covered by a shutter, in particular an automatic one. Therein, several sample containers 14 can simultaneously be seen in the removal station 20 and can be taken out in parallel. The second conveyer 27 is visible in the flat housing 12b through the opening 22.

An opening 34 to the treating apparatus 12, i.e. the above mentioned centrifuge for the sample containers 14 with an analysis sample P each to be treated, is arranged between the first and the second conveyer 26, 27. The transfer device 44 takes the sample containers 14 from the first conveyer 26 and hands them over through the opening 34 to the treating apparatus 12. After treatment, the transfer device 44 takes the sample containers 14 out of the treating apparatus 12 and passes them over to the second conveyer 27.

The first and the second conveyer 26, 27 are embodied as horizontally circulating conveyer tracks 26a, 27a. The conveyer track 26a of the first conveyer 26 extends from the input station 18 to the transfer device 44 and back again. The conveyer track 27a of the second conveyer 27 extends from the removal station 20 to the input station 44 and back again. The removal station 20 is elongated in the conveying direction 27b such that multiple sample containers 14 with an analysis sample P to be treated can be seen on the length L of the removal station 20.

The first and the second conveyer 26, 27 can be formed, for example, by a link chain or a conveyer belt having open recesses on top for taking up the sample containers 14 with an analysis sample P to be treated.

In this embodiment, the input station 18 is arranged displaced upwards and, with reference to the first conveyer 26, obliquely to the conveying direction 26b, and it is connected to the first conveyer 26 through a transfer conveyer 28 for sample containers 14 with the analysis sample P. The sample container 14 with the analysis sample P is moved through the transfer conveyer 28 from the input station 18 to the first conveyer 26. In case of a vertical upwards displacement V1 with respect to the conveying direction 26b of the first conveyer 26, the transfer conveyer 28 is formed by a drop-down passage 30. The input station 18 is, furthermore, horizontally displaced with respect to the removal station 20, see displacement V2.

For positioning the respective sample container 14 with the analysis sample P at the input station 18, an insertion adapter 32 is provided into which the sample container 14 with the analysis sample P can be inserted from above and can be positioned thereby. The insertion adapter 32 is formed by a tube shaped receiving portion 34 extending upwards and having a lateral window 36, for example an opening, for the identification K. The identification K is arranged in such a position on the sample container 14 that the identification K is located in the area of the window 36 in the state where the sample container 40 is inserted into the insertion adapter 32. An identification unit 38, for example a pistol-like one, is arranged opposite to the window 36, preferably in the left front corner area of the device 10. The identification unit 38 can, for example, be a reader and can be selectively inserted into and removed from a holder 40. Alternatively, the identification unit 38 can also be fixedly installed, i.e. permanently implemented. The insertion adapter 32 can, for example, extend upwards from a base 42.

The bottom of the insertion adapter 32 may be opened and closed by a closure means 50 controlled by a control device (not shown) such that the sample container gets over the drop-down passage 30 into the first conveyer 26 upon opening of the closure means 50.

The first conveyer 26 is driven by a motor 36, and the second conveyer 27 is driven by a motor 48. The conveyers are guided across a large number of friction wheels 52 and 54 in order to form conveyers 26, 27 as long as possible. Thereby, an intermediate storage is generated but also a kind of buffer for the treating apparatus 12.

In the following, the function of the device 10 is described by cooperating with the treating apparatus 12.

An analysis sample P to be treated, is input into a sample container 14. The sample container 14 is handed over to the device 10 by an operator by handover at the input station 18 whereby the sample container 14 is inserted into the insertion adapter 32. Thereafter, the identification K of the sample container 14 is identified by the identification unit 38. If the identification is not recognized, the operator has to align the sample container 14 such that the identification K is detected. Only thereafter, the sample container 14 is transferred over the drop-down passage 30 of the transfer conveyer 28 to the first conveyer 26 by opening the closure means 50. The sample container 14 is then fed to the transfer device 44 and, ultimately, to the treating apparatus 12 by means of the first conveyer 26.

After treatment in the treating apparatus 12, the sample container 14 is fed onto the second conveyer 27 and thereby again to the removal station 20 where the sample container 14 with the analysis sample P can be removed.

By arranging the conveyers as circulating endless conveyers, differing sequences in processing the sample containers become possible. The processing can be carried out at random, according to predetermined priorities, having regard to the treating steps and the like. The control of the sequence is taken over by a control device which cooperates with the identification unit 38.

By identifying the respective sample containers 14 with an analysis sample P to be treated, prior to the insertion thereof into the first conveyer 26, a controlled feeding of the sample containers 14 with the analysis sample P is, furthermore, ensured in a simple manner. Uncontrolled erroneous runs of the sample containers 14 are avoided from the beginning.

The following steps after the transfer of the sample containers 14 with the analysis sample P to the input station 18 up to the presentation at the removal station 20 are, preferably, carried out automatically. The control device serves this purpose.

It is to be understood that the above description is intended to be illustrative and not restrictive. Many embodiments will be apparent to those skilled in the art upon reviewing the above description. The scope of the invention should, therefore, be determined not as reference to the above description, but should instead be determined with reference to the appended claims along with the full scope of equivalence to which such claims are entitled.

What is claimed is:

1. Device for feeding sample containers to a treating apparatus for treating said samples residing in said containers, comprising:
   an input station;
   a first conveyor;
   a transfer device;
   a second conveyor;
   a removal station;
   said treating apparatus is a centrifuge;
   said input station transfers each of said sample containers to said first conveyor;
   said first conveyor transports each of said sample containers to said transfer device;
   said transfer device removes each of said sample containers out of said first conveyor and transfers each of said sample containers to said treating apparatus;
   after treatment, said transfer device removes each of said sample containers out of said treating apparatus and transfers each of sample containers to said second conveyor;
   said second conveyer conveys each of said sample containers to said removal station for removing each of said sample containers out of said conveyer;
   an identification unit for identifying each of said sample containers;

wherein said first and second conveyers are configured for receiving sample containers and form circulating endless conveyer tracks; and, wherein said input station is displaced obliquely with respect to said conveying direction of said first conveyer.

2. Device for feeding carriers of sample containers to a treating apparatus for treating said samples residing in said containers, comprising:
- an input station;
- a first conveyor;
- a transfer device;
- a second conveyor;
- a removal station;
- said treating apparatus is a centrifuge;
- said input station transfers at least one carrier of sample containers to said first conveyor;
- said first conveyor transports said at least one carrier of sample containers to said transfer device;
- said transfer device removes said at least one carrier of sample containers out of said first conveyor and transfers said at least one carrier of sample containers to said treating apparatus;
- after treatment, said transfer device removes said at least one carrier of sample containers out of said treating apparatus and transfers at least one carrier of sample containers to said second conveyor;
- said second conveyer conveys said at least one carrier of sample containers to said removal station for removing said at least one carrier of sample containers out of said conveyer;
- an identification unit for identifying said at least one carrier of sample containers;
- wherein said first and second conveyers are configured for receiving said at least one carrier of sample containers and form circulating endless conveyer tracks; and,
- wherein said input station is displaced obliquely with respect to said conveying direction of said first conveyer.

3. Device according to claim 1, wherein said first conveyer runs from said input station to said transfer device.

4. Device according to claim 1, wherein said second conveyer runs from said transfer device to said removal station.

5. Device according to claim 1, wherein said conveyer comprises receiving means for receiving single sample containers.

6. Device according to claim 5, wherein said receiving means for said sample container is arranged in a line.

7. Device according to claim 1, wherein a transfer conveyer is provided for conveying each of said sample containers from said input station to said first conveyer.

8. Device according to claim 7, wherein said identification unit is arranged in the area of said transfer conveyer and said identification unit cooperates with said transfer conveyer such that each of said sample containers is conveyed to said first conveyer only after its identification.

9. Device according to claim 1, wherein said input station (18) is displaced upwards with respect to said first and second conveyors and/or said removal station.

10. Device according to claim 1, wherein said transfer conveyer is formed by a drop-down passage (30).

11. Device according to claim 1, wherein said identification unit is arranged in the vicinity of said input station.

12. Device according to claim 1, wherein an adapter for inserting said sample container is provided at said input station, and, wherein said adapter is adapted to the outer shape of said sample container.

13. Device according to claim 12, wherein said adapter is formed by a tube-like receiving part.

14. Device according to claim 13, wherein said adapter is provided with a lateral window for identification of said sample container by said identification unit.

15. Device according to claim 14, wherein said identification unit is arranged opposite to said window.

16. Device according to claim 15, wherein said identification unit is formed by a reader.

17. Device according to claim 15, wherein a holder is provided within which said identification unit is supported and from which said identification unit is selectively removable.

18. Device according to claim 16, wherein a holder is provided within which said identification unit is supported and from which said identification unit is selectively removable.

* * * * *

UNITED STATES PATENT AND TRADEMARK OFFICE
CERTIFICATE OF CORRECTION

PATENT NO. : 8,220,617 B2
APPLICATION NO. : 12/490308
DATED : July 17, 2012
INVENTOR(S) : Klaus-Gunter Eberle Page 1 of 1

It is certified that error appears in the above-identified patent and that said Letters Patent is hereby corrected as shown below:

On the Title Page item [57], in the Abstract, line 13, after "direction (26b, 27b)" delete "Hof" and insert --of--.

Signed and Sealed this
Fourth Day of September, 2012

David J. Kappos
*Director of the United States Patent and Trademark Office*